(12) United States Patent
Fukuzumi et al.

(10) Patent No.: US 7,977,486 B2
(45) Date of Patent: Jul. 12, 2011

(54) QUINOLINIUM ION DERIVATIVES, PROCESS FOR THE PRODUCTION OF THE DERIVATIVES, PRODUCTS MADE BY USING THE SAME, AND REDUCTION AND OXIDATION METHODS WITH THE DERIVATIVES

(75) Inventors: Shunichi Fukuzumi, Suita (JP); Hiroaki Kotani, Suita (JP); Kei Ohkubo, Suita (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 12/440,538

(22) PCT Filed: Mar. 5, 2007

(86) PCT No.: PCT/JP2007/054152
§ 371 (c)(1),
(2), (4) Date: May 22, 2009

(87) PCT Pub. No.: WO2008/029523
PCT Pub. Date: Mar. 13, 2008

(65) Prior Publication Data
US 2010/0004454 A1    Jan. 7, 2010

(30) Foreign Application Priority Data
Sep. 8, 2006   (JP) .................................. 2006-243643

(51) Int. Cl.
*C07D 215/04*  (2006.01)
*C07D 213/22*  (2006.01)
*C07D 213/56*  (2006.01)

(52) U.S. Cl. .......................... 546/173; 546/257; 546/316

(58) Field of Classification Search .................. 546/173, 546/257, 316
See application file for complete search history.

(56) References Cited

U.S. PATENT DOCUMENTS
5,532,374 A    7/1996  Lee et al.

FOREIGN PATENT DOCUMENTS
JP    9-118667    5/1997
JP    2003-128641  5/2003

OTHER PUBLICATIONS

Ohkubo et al. Chem. Comm. 2005, 4520-4522, col. A of p. 4520.*
Cody, STN Accession No. 1985:158452 Document No. 102:158452 Abstract of Acta Crystallographica, Section C: Crystal Structure Communications (1985), C41(3), 413-15.*
SORST, The Chemical Society of Japan Dai 86 Kai Shunki Nenkai 2006 Nen Koen Yokoshu I, Mar. 13, 2006, p. 1296, Abstract No. 1, K4—36.*
Mueller et al. STN Accession No. 1950:30168 Document No. 44:30168 Abstract of Journal of the American Chemical Society (1950), 72,1598-9.*
Abramovitch et al. STN Abstracts of Journal of the Chemical Society (1954) 3839-41.*
Moiseev et al. STN Abstracts of Chemistry of Heterocyclic Compounds (NewYork)(Translation of Khimiya Geterotsiklicheskikh Soedinenii) (2000), 36(4), 439-442.*
Volchkov et al. STN Abstracts of Journal of Fluorescence (2000), 10(2), 161-165.*
Fukuzumi, et al., "Electron-Transfer State of 9-Mesityl-10-methylacridinjum Ion with a Much Longer Lifetime and Higher Energy Than That of the Natural Photosynthetic Reaction Center", J. Am. Chem. Soc., vol. 126, No. 6, 2004, pp. 1600-1601.
Ohkubo, et al., "Misleading effects of impurities derived from the extremely long-lived electron-transfer state of 9-mesityl-10-methylacridinium ion", Chem. Commun., 2005, 4520-4522.
Kotani, et al., "Formation of Long-Lived Electron-Transfer State and Detection of the π-Dimer Radical Cation Using Doner-Acceptor Linked Dyads", The abstracts of the 86th Annual Spring Meeting of the Chemical Society of Japan, 1K4-36, Mar. 2006.
Miyoshi, et al., "Probing the Ubiquinone Reduction Site Mitochondrial Complex I using Novel Cationic Inhibitors", The Journal of Biological Chemistry, vol. 272, No. 26, Jun. 1997, pp. 16176-16183.
Quast, et al., "Ring Expansion of 2-Alkylidenedihydroquinolines to 2-Iminodihydro-l-benzazepines by Phenyl , Methanesulphonyl, and Trifluoromethanesulphonyl Azide", Eur. J. Org. Chem, No. 3, 2000, pp. 507-520.
Nesvadba, et al., "Oxidative Elimination of Phenyl Group from α Position of Quaternary Quinolinium Salts", Colloction Czechoslovak Chem. Commun., vol. 48, No. 10, 1983, pp. 2965-2969.

(Continued)

*Primary Examiner* — Nizal Chandrakumar
(74) *Attorney, Agent, or Firm* — Hamre, Schumann, Mueller & Larson, P.C.

(57) ABSTRACT

An electron donor-acceptor dyad is provided that can provide a charge-separated state with longevity and not only high oxidizing power but also high reducing power. A compound of the present invention is a quinolinium ion derivative represented by the following formula (I), a stereoisomer or tautomer thereof, or a salt thereof:

[Chemical Formula 1]

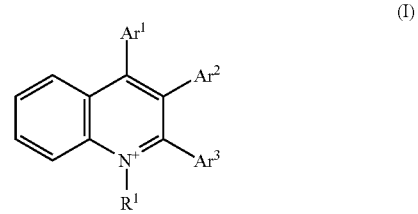

(I)

where $R^1$ is a hydrogen atom or an alkyl group, and $Ar^1$ to $Ar^3$ each are a hydrogen atom or an electron-donating group. The compound of the present invention has the above-mentioned structure and therefore can provide a charge-separated state with longevity and not only high oxidizing power but also high reducing power and can be used for various products such as photocatalysts, photosensitizers, dyes, oxidants, reductants, dye-sensitized solar cells, and organic EL devices.

1 Claim, 1 Drawing Sheet

OTHER PUBLICATIONS

Tokarev, et al., Corrosion Inhibitors of Metals Based on the Coking Products Quinoline and Isoquinoline, Zashchita Metallov, vol. 12, No. 5, 1976, pp. 620-622.

Digregorio, "Chromatographic separation of 2-phenylquinoline analogues", Journal of Chromatography, vol. 90, No. 2, 1974, pp. 396-398.

Katritzky, et al., A Novel Synthesis of Quinolinium Salts via Benzotriazole Methodology, J. Heterocyclic Chem., vol. 35, No. 2, 1998, pp. 467-470.

Tomisawa, et al., "Studies on 1-Alkyl-2(1*H*)-pyridone Derivatives. XVIII. Reaction of 1-Methyl-2(1*H*)-quinolone with Phosphoryl Chloride and N, N-Dimethylaniline", Chem. Pharm. Bull., vol. 21, No. 12, 1973, pp. 2602-2606.

Julius, et al., The constitutional factor in cinchophen conditioning pharmacological activity, Ber. 60B, 1927, pp. 1253-1257, Chemical Abstracts, vol. 21, 269c-g, Abstract No. 21:21909.

Julius, et al., Benzopolymethylene compounds. III. Dehydrogenation experiments with tetralin, hydrindene and tetrahydroacenaphthene (tetraphthene) derivatives, Ber. 55B, 1922, pp. 1687-1700, Chemical Abstracts, vol. 16, 4201b-i, 4202a-d, Abstract No. 16:24681.

Jacobi, et al., "Oxidation of aryl-substituted cycloheptatrienes by photoinduced electron transfer", J. Chem. Soc., Perkin Trans. 2: Physical Organic Chemistry No. 8, 1999, pp. 1695-1702.

\* cited by examiner

QUINOLINIUM ION DERIVATIVES, PROCESS FOR THE PRODUCTION OF THE DERIVATIVES, PRODUCTS MADE BY USING THE SAME, AND REDUCTION AND OXIDATION METHODS WITH THE DERIVATIVES

TECHNICAL FIELD

The present invention relates to quinolinium ion derivatives, processes for producing the derivatives, products produced using the derivatives, and reduction and oxidization methods using the derivatives.

BACKGROUND ART

Examples of electron donor-acceptor dyads reported conventionally include a number of dye molecules such as porphyrin, and the charge-separated states thereof have been reported. From the viewpoint of industrial applicability, these electron donor-acceptor dyads are required to have properties such as longevity, high oxidizing power, and high reducing power for the charge-separated state. In order further to improve the properties, further studies have been made.

However, from the viewpoint of industrial applicability, no electron donor-acceptor dyad with sufficient reducing power has been reported yet. Therefore, among the aforementioned respective properties of the electron donor-acceptor dyads, improvement of the reducing power is an important study subject. For instance, examples of the electron donor-acceptor dyad that provides a charge-separated state having the longest longevity so far include a 9-mesityl-10-methylacridinium ion (see Nonpatent Documents 1 and 2). However, the electron-transfer state (charge-separated state) has low energy and therefore the reducing power thereof is not so strong, which has been a problem.

[Nonpatent Document 1] S. Fukuzumi, H. Kotani, K. Ohkubo, S. Ogo, N. V. Tkachenko, H. Lemmetyinen, J. Am. Chem. Soc., 2004, 126, 1600

[Nonpatent Document 2] K. Ohkubo, H. Kotani, S. Fukuzumi, Chem. Commun. 2005, 4520.

DISCLOSURE OF INVENTION

Accordingly, the present invention is intended to provide an electron donor-acceptor dyad that can provide a charge-separated state with longevity and not only high oxidizing power but also high reducing power. Furthermore, the present invention provides a process for producing the electron donor-acceptor dyad. Moreover, the present invention provides products and reduction and oxidation methods, in each of which such an electron donor-acceptor dyad is used.

In order to solve the aforementioned problems, the present inventors focused on quinolinium ions with a low reduction potential and made keen studies assiduously. As a result, the present inventors found that an electron donor-acceptor dyad was able to be obtained that was capable of providing a charge-separated state with longevity and not only high oxidizing power but also high reducing power by binding an electron-donating site to a pyridine ring site of a quinolinium ion.

The compound of the present invention is a quinolinium ion derivative represented by the following formula (I), a stereoisomer or tautomer thereof, or a salt thereof.

[Chemical Formula 10]

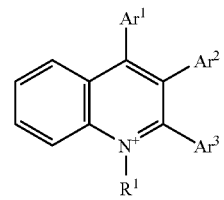

In the above-mentioned formula (I), $R^1$ is a hydrogen atom, an alkyl group, a carboxyalkyl group, which is an alkyl group with a carboxyl group added to the end thereof, an aminoalkyl group, which is an alkyl group with an amino group added to the end thereof, or a polyether chain.

$Ar^1$ to $Ar^3$ each are a hydrogen atom or an electron-donating group, they may be identical to or different from one another, and at least one of $Ar^1$ to $Ar^3$ is an electron-donating group.

However, the case is excluded where $R^1$ is an ethyl group, $Ar^1$ and $Ar^3$ each are a phenyl group, and $Ar^2$ is a hydrogen atom, a methyl group, or a phenyl group.

A production process of the present invention is a process for producing a quinolinium ion derivative represented by the above-mentioned formula (I), a stereoisomer or tautomer thereof, or a salt thereof, and includes reacting a quinoline derivative represented by the following formula (II) with a compound represented by the following formula (III).

[Chemical Formula 11]

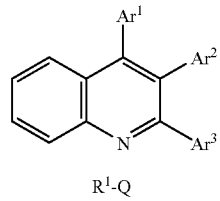

In the aforementioned formula (II), $Ar^1$ to $Ar^3$ are the same as those of the aforementioned formula (I).

In the aforementioned formula (III), $R^1$ is the same as that of the aforementioned formula (I), and Q is an electron-withdrawing group.

A product of the present invention is a product that is used as a photocatalyst, a photosensitizer, a dye, an oxidant, a reductant, a cell, a dye-sensitized solar cell, or an organic EL device. The photocatalyst, photosensitizer, dye, oxidant, reductant, cell, dye-sensitized solar cell, and organic EL device of the present invention each contain a quinolinium ion derivative represented by the following formula (I'), a stereoisomer or tautomer thereof, or a salt thereof.

[Chemical Formula 12]

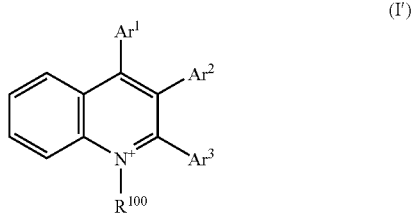

In the aforementioned formula (I'), $R^{100}$ is a hydrogen atom or an arbitrary substituent.

$Ar^1$ to $Ar^3$ each are a hydrogen atom or an electron-donating group, they may be identical to or different from each other, and at least one of $Ar^1$ to $Ar^3$ is an electron-donating group.

The reduction method of the present invention is:

a method for reducing a substance to be reduced using a quinolinium ion derivative represented by the aforementioned formula (I'), a stereoisomer or tautomer thereof, or a salt thereof, wherein the method includes producing an excited species in an electron-transfer state (charge-separated state) by exciting a quinolinium ion derivative represented by the aforementioned formula (I'), a stereoisomer or tautomer thereof, or a salt thereof through photoirradiation, and reducing the substance to be reduced by transferring an electron from the excited species to the substance to be reduced.

The oxidation method of the present invention is:

a method for oxidizing a substance to be oxidized using a quinolinium ion derivative represented by the aforementioned formula (I'), a stereoisomer or tautomer thereof, or a salt thereof, wherein the method includes producing an excited species in an electron-transfer state (charge-separated state) by exciting a quinolinium ion derivative represented by the aforementioned formula (I'), a stereoisomer or tautomer thereof, or a salt thereof through photoirradiation, and oxidizing the substance to be oxidized by transferring an electron from the substance to be oxidized to the excited species.

The quinolinium ion derivative represented by the aforementioned formula (I'), stereoisomer or tautomer thereof, or salt thereof (hereinafter, also referred simply as a "compound (I')") is an electron donor-acceptor dyad with the aforementioned structure and thereby can provide a charge-separated state with longevity and not only high oxidizing power but also high reducing power. As described above, this was found by the present inventors as a result of studies made assiduously.

The compound (I') can be used suitably for a reductant to provide a high reducing power. Furthermore, since the compound (I') has not only the high reducing power but also longevity and high oxidizing power for the charge-separated state, it is applicable to various products such as photocatalysts, photosensitizers, dyes, oxidants, cells, dye-sensitized solar cells, and organic EL devices. For example, when the compound (I') is combined with a platinum catalyst, a hydrogen-evolving photocatalyst can be obtained. Moreover, when the cells of the present invention contain the compound (I') as a dye, they also can be used as dye-sensitized solar cells. All these applications relate to the inventions made by the present inventors.

In the reduction method of the present invention, since the use of the compound (I') makes it possible to obtain a charge-separated state with both longevity and high reducing power, the reduction method also is applicable to a substance to be reduced that requires high reducing power. Similarly, in the oxidation method of the present invention, since the use of the compound (I') makes it possible to obtain a charge-separated state with both longevity and high oxidizing power, the oxidation method also is applicable to a substance to be oxidized that requires high oxidizing power. Furthermore, since the reduction and oxidation methods of the present invention allow the compound (I') to be excited through photoirradiation and thereby reducing power or oxidizing power to be produced, they can be performed easily.

Among compounds (I'), the quinolinium ion derivative represented by the aforementioned formula (I), stereoisomer or tautomer thereof, or salt thereof (hereinafter, also referred to simply as a "compound of the present invention") is a new compound invented by the present inventors. The compound of the present invention can be produced by the aforementioned production process of the present invention, but the production process is not limited thereto and it can be produced by any process. Furthermore, the compound of the present invention is not limited to the aforementioned respective applications and may be used for any applications.

BEST MODE FOR CARRYING OUT THE INVENTION

Figure 1:
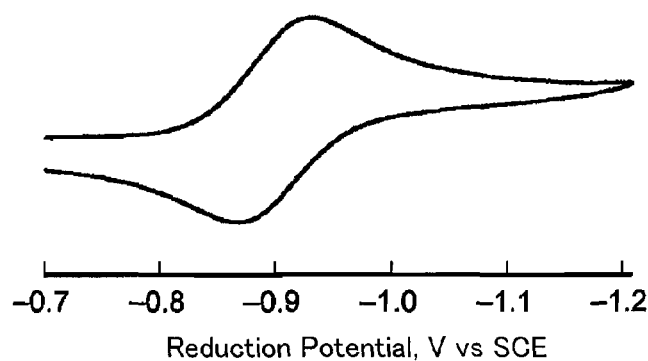
FIG. 1 is a diagram showing an example of reduction waves (cyclic voltammogram) of a quinolinium ion derivative according to the present invention.

Next, embodiments of the present invention are described. In the present invention, when the scope of the invention is limited by numerical values, not only the case of the exact range of the numerical values but also the case of an approximate range of the numerical values is embraced. For example, the case of "100 to 200° C." embraces not only the exact range of 100 to 200° C. but also a range of about 100° C. to about 200° C. Furthermore, for example, a description "the number of carbon atoms is 1 to 6" embraces both an exact range of 1 to 6 and a range of about 1 to 6.

[Compound of the Present Invention]

As described above, the compound of the present invention is a quinolinium ion derivative represented by the aforementioned formula (I), a stereoisomer or tautomer thereof, or a salt thereof. The following descriptions include a preferable structure of the compound of the present invention.

In the aforementioned formula (I), it is preferable that $R^1$ be, for example, a hydrogen atom, a linear or branched alkyl group having a carbon number of 1 to 6, a linear or branched alkyl group having a carbon number of 1 to 6 with a carboxyl group added to the end thereof, a linear or branched alkyl group having a carbon number of 1 to 6 with an amino group added to the end thereof, or a polyethylene glycol (PEG) chain. The PEG chain is an example of the above-mentioned polyether chain, but the type of the polyether chain is not limited thereto and any polyether chain may be used. In $R^1$, the degree of polymerization of the polyether chain is not particularly limited and is, for example, 1 to 100, preferably 1 to 50, and more preferably 1 to 10. In the case where the polyether chain is a PEG chain, the degree of polymerization is not particularly limited and is, for example, 1 to 100, preferably 1 to 50, and more preferably 1 to 10. Furthermore, $Ar^1$ to $Ar^3$ each are preferably, for example, a hydrogen atom, an alkyl group, or an aromatic ring, and it is more preferable that the alkyl group be a linear or branched alkyl group having a carbon number of 1 to 6. In $Ar^1$ to $Ar^3$, the aromatic ring further may have one or plural substituents on the ring and in the case of the plural substituents, they may be identical to or different from each other.

In the aforementioned formula (I), in $Ar^1$ to $Ar^3$, it is more preferable that the aromatic ring be, for example, a benzene ring, a naphthalene ring, an anthracene ring, a phenanthrene ring, a pyridine ring, a thiophene ring, or a pyrene ring. Furthermore, in $Ar^1$ to $Ar^3$, the substituent on the aromatic ring is more preferably an alkyl group, an alkoxy group, any one of primary to tertiary amines, a carboxylic acid, or a carboxylate ester, and further preferably a linear or branched alkyl group having a carbon number of 1 to 6, a linear or branched alkoxy group having a carbon number of 1 to 6, one of primary to tertiary amines, a carboxylic acid, or a carboxylate ester. The secondary amine is not particularly limited and is preferably, for example, an alkylamino group and more preferably a linear or branched alkylamino group having a carbon number of 1 to 6. The tertiary amine is not particularly limited and is preferably, for example, a dialkylamino group and more preferably a dialkylamino group with a linear or branched alkyl group having a carbon number of 1 to 6.

In the substituent on the aromatic ring in $Ar^1$ to $Ar^3$, "carboxylic acid" denotes a carboxyl group or a group with a carboxyl group added to the end thereof (for example, a carboxyalkyl group), and "carboxylate ester" denotes a carboxylate ester group such as an alkoxycarbonyl group or a phenoxycarbonyl group and an acyloxy group. The alkyl group in the carboxyalkyl group is preferably, for example, a linear or branched alkyl group having a carbon number of 1 to 6. The alkoxy group in the alkoxycarbonyl group is preferably, for example, a linear or branched alkoxy group having a carbon number of 1 to 6.

Among quinolinium ion derivatives represented by the aforementioned formula (I), particularly preferable one from the viewpoints of, for example, the longevity, high oxidizing power, and high reducing power of the charge-separated state is, for example, a quinolinium ion derivative represented by any one of the following formulae 1 to 5.

[Chemical Formula 13]

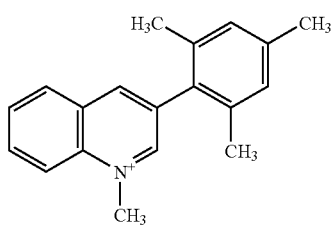

1

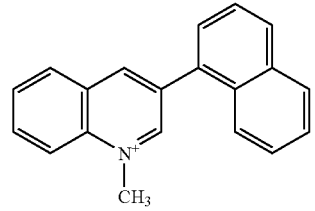

2

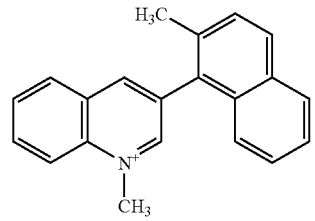

3

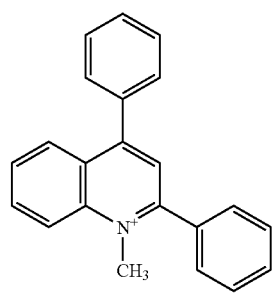

4

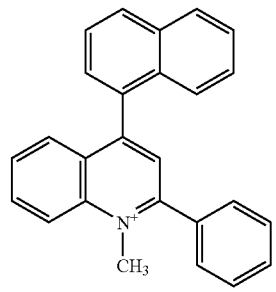

5

Besides the above-mentioned compounds 1 to 5, for example, compounds 6 to 36 indicated in the following table 1 are particularly preferable. In the following tables 1 and 2, the structures of the compounds 6 to 36 are indicated in combination with $R^1$ and $Ar^1$ to $Ar^3$ in the aforementioned formula (I). Furthermore, with reference to the examples described later, persons skilled in the art can produce and use those compounds 6 to 36 easily according to the compounds 1 to 5 without, for example, undue trial and error or complicated and advanced experiments.

TABLE 1

| Compound | Substituent | | | |
| --- | --- | --- | --- | --- |
| No. | $R^1$ | $Ar^1$ | $Ar^2$ | $Ar^3$ |
| 6 | Methyl Group | Hydrogen Atom | Phenyl Group | Hydrogen Atom |
| 7 | Methyl Group | Hydrogen Atom | Tolyl Group | Hydrogen Atom |
| 8 | Methyl Group | Hydrogen Atom | Xylyl Group | Hydrogen Atom |
| 9 | Methyl Group | Hydrogen Atom | Durenyl Group | Hydrogen Atom |
| 10 | Methyl Group | Hydrogen Atom | Phenyl Group | Hydrogen Atom |
| 11 | Methyl Group | Hydrogen Atom | Aminophenyl Group | Hydrogen Atom |
| 12 | Methyl Group | Hydrogen Atom | Methoxynaphthyl Group | Hydrogen Atom |
| 13 | Methyl Group | Hydrogen Atom | Anthryl Group | Hydrogen Atom |
| 14 | Methyl Group | Hydrogen Atom | Pyrenyl Group | Hydrogen Atom |

TABLE 1-continued

| Compound | Substituent | | | |
|---|---|---|---|---|
| No. | R¹ | Ar¹ | Ar² | Ar³ |
| 15 | Ethoxycarbonyl Group | Hydrogen Atom | Phenyl Group | Hydrogen Atom |
| 16 | Ethoxycarbonyl Group | Hydrogen Atom | Tolyl Group | Hydrogen Atom |
| 17 | Ethoxycarbonyl Group | Hydrogen Atom | Xylyl Group | Hydrogen Atom |
| 18 | Ethoxycarbonyl Group | Hydrogen Atom | Durenyl Group | Hydrogen Atom |
| 19 | Ethoxycarbonyl Group | Hydrogen Atom | Phenyl Group | Hydrogen Atom |
| 20 | Ethoxycarbonyl Group | Hydrogen Atom | Methoxynaphthyl Group | Hydrogen Atom |
| 21 | Ethoxycarbonyl Group | Hydrogen Atom | Anthryl Group | Hydrogen Atom |
| 22 | Ethoxycarbonyl Group | Hydrogen Atom | Pyrenyl Group | Hydrogen Atom |

TABLE 2

| Compound | Substituent | | | |
|---|---|---|---|---|
| No. | R¹ | Ar¹ | Ar² | Ar³ |
| 23 | Ethoxycarbonyl Group | Hydrogen Atom | Mesityl Group | Hydrogen Atom |
| 24 | Ethoxycarbonyl Group | Hydrogen Atom | Naphthyl Group | Hydrogen Atom |
| 25 | Ethoxycarbonyl Group | Hydrogen Atom | Methylnaphthyl Group | Hydrogen Atom |
| 26 | Methyl Group | Aminophenyl Group | Hydrogen Atom | Phenyl Group |
| 27 | Methyl Group | Tolyl Group | Hydrogen Atom | Phenyl Group |
| 28 | Methyl Group | Xylyl Group | Hydrogen Atom | Phenyl Group |
| 29 | Methyl Group | Durenyl Group | Hydrogen Atom | Phenyl Group |
| 30 | Methyl Group | Phenyl Group | Hydrogen Atom | Phenyl Group |
| 31 | Methyl Group | Methoxynaphthyl Group | Hydrogen Atom | Phenyl Group |
| 32 | Methyl Group | Anthryl Group | Hydrogen Atom | Phenyl Group |
| 33 | Methyl Group | Pyrenyl Group | Hydrogen Atom | Phenyl Group |
| 34 | Methyl Group | Mesityl Group | Hydrogen Atom | Phenyl Group |
| 35 | Methyl Group | (N,N-dimethylamino) Phenyl Group | Hydrogen Atom | Phenyl Group |
| 36 | Methyl Group | Phenyl Group | Phenyl Group | Phenyl Group |

When the quinolinium ion derivative represented by the aforementioned formula (I) has an isomer such as a tautomer or a stereoisomer (for example, a geometric isomer, a conformer, or an optical isomer), such an isomer also is included in the compounds of the present invention. Furthermore, the salt of the quinolinium ion derivative represented by the aforementioned formula (I) or an isomer thereof also is included in the compounds of the present invention. The salt may be an acid addition salt but it also may be a base addition salt when the quinolinium ion derivative represented by the aforementioned formula (I) or an isomer thereof can form a base addition salt. Furthermore, the acid that forms the acid addition salt may be an inorganic acid or an organic acid, and the base that forms the base addition salt may be an inorganic base or an organic base. The inorganic acid is not particularly limited. Examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited. Examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited. Examples thereof include ammonium hydroxide, alkali metal hydroxide, alkaline earth metal hydroxide, carbonate, and hydrogen carbonate. More specific examples include sodium hydroxide, potassium hydroxide, potassium carbonate, sodium carbonate, sodium bicarbonate, potassium bicarbonate, calcium hydroxide, and calcium carbonate. The organic base also is not particularly limited.

Examples thereof include ethanolamine, triethylamine, and tris(hydroxymethyl)aminomethane. The method of producing these salts also is not particularly limited. They each can be produced by a method in which, for example, the acids or bases as described above each are added suitably to the quinolinium ion derivative represented by the aforementioned formula (I) or an isomer thereof by a known method. Furthermore, when an isomer exists in $R^1$ and $Ar^1$ to $Ar^3$ in the aforementioned formula (I), it can be any isomer. For instance, in the case of a "naphthyl group", it may be a 1-naphthyl group or a 2-naphthyl group.

Furthermore, in the compound of the present invention, the absorption band is not particularly limited, but it is preferable that the compound have an absorber in a visible region. This is because, when it has an absorption band in the visible region, visible light excitation can be used. Since this allows sunlight to be used as an energy source, the compound also is applicable to, for example, solar cells.

Furthermore, in the present invention, the alkyl group is not particularly limited. Examples thereof include a methyl group, an ethyl group, an n-propyl group, an isopropyl group, an n-butyl group, an isobutyl group, a sec-butyl group, and a tert-butyl group, as well as groups (for example, an alkylamino group and an alkoxy group) containing alkyl groups in their structures. Moreover, the perfluoroalkyl group is not particularly limited. Examples thereof include perfluoroalkyl groups derived from a methyl group, an ethyl group, an n-propyl group, an isopropyl group, an n-butyl group, an isobutyl group, a sec-butyl group, and a tert-butyl group, as well as groups containing perfluoroalkyl groups in their structures (for example, a perfluoroalkylsulfonyl group and a perfluoroacyl group). In the present invention, the acyl group is not particularly limited. Examples thereof include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group, as well as groups containing acyl groups in their structures (for example, an acyloxy group and an alkanoyloxy group). In the present invention, carbonyl carbon is included in the carbon number of the acyl group. For example, an alkanoyl group (an acyl group) with a carbon number of 1 indicates a formyl group. Furthermore, in the present invention, a "halogen" denotes an arbitrary halogen element, and examples thereof include fluorine, chlorine, bromine, and iodine.

[Production Process of the Present Invention]

Next, the production process of the present invention is described.

As described above, the production process of the present invention is a process for producing a compound of the present invention (a quinolinium ion derivative represented by the aforementioned formula (I), a stereoisomer or tautomer thereof, or a salt thereof) and includes reacting a quinoline derivative represented by the following formula (II) with a compound represented by the following formula (III).

[Chemical Formula 14]

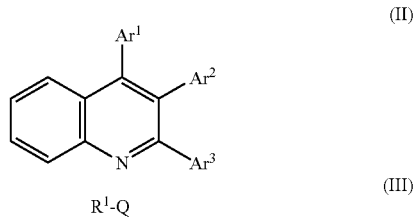

In the aforementioned formula (II), $Ar^1$ to $Ar^3$ are the same as those of the aforementioned formula (I).

In the aforementioned formula (III), $R^1$ is the same as that of the aforementioned formula (I), and Q is an electron-withdrawing group.

In the aforementioned formula (III), Q is not particularly limited as long as it is an electron-withdrawing group. Examples thereof include a halogen, perfluoroalkyl group, perfluoroalkylsulfonyl group, and perfluoroacyl group, and particularly, fluorine, chlorine, bromine, iodine, a trifluoromethyl group, a trifluoromethylsulfonyl group, and a trifluoromethylcarbonyl group are more preferable.

Conditions for the reaction between a quinoline derivative represented by the aforementioned formula (II) and a compound represented by the aforementioned formula (III) are not particularly limited and can be set suitably with reference to, for example, conditions for known similar reactions. The ratio in amount (molar ratio) between the quinoline derivative (II) and the compound (III) is not particularly limited and is, for example, 1:1 to 1:10, preferably 1:1 to 1:4, and particularly preferably 1:1. Furthermore, for example, a reactant or solvent other than the quinoline derivative (II) and compound (III) may or may not be used suitably as required. The solvent is not particularly limited and may be, for example, water or an organic solvent. Examples of the organic solvent include halogenated solvents such as methylene chloride, chloroform, and carbon tetrachloride, ketones such as acetone, and nitrile solvents such as acetonitrile. These solvents may be used independently or two or more of them may be used in combination. When a solvent is used, the concentration of the quinoline derivative (II) is not particularly limited and is, for example, 0.01 to 0.2 mol/L, preferably 0.02 to 0.1 mol/L, and more preferably 0.03 to 0.05 mol/L. The reaction temperature is not particularly limited and is, for example, 0 to 80° C., preferably 10 to 40° C., and more preferably 20 to 30° C. The reaction time also is not particularly limited and is, for example, 10 to 40 hours, preferably 20 to 30 hours, and more preferably 25 to 30 hours.

Furthermore, after production of quinolinium ions, an anion-exchange process may be performed as required. The method of the anion-exchange process is not particularly limited and an arbitrary method can be used as required. Examples of substances that are applicable to the anion-exchange process include perhalogen acids such as perfluoric acid, perchloric acid, perbromic acid, and periodic acid, as well as boron tetrafluoride and phosphorus hexafluoride. They may be used independently or two or more of them may be used in combination. Moreover, for example, a reactant or solvent other than those described above may or may not be used suitably as required.

The process for producing a quinoline derivative represented by the aforementioned formula (II) is not particularly limited, but it is preferable that the quinoline derivative be produced by a first production process in which a halogenated quinoline represented by the following formula (IV) is reacted with a boronic acid ester represented by the following formula (V).

[Chemical Formula 15]

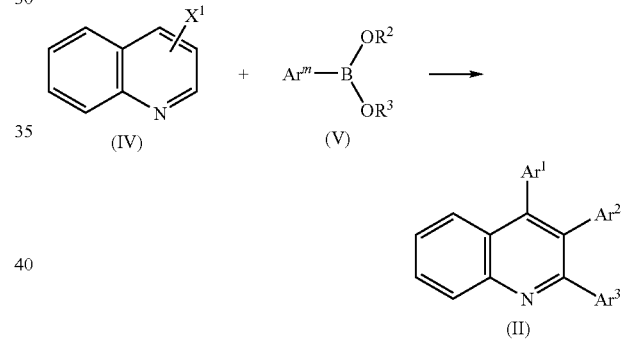

In the above formula (IV), $X^1$ is a halogen group on a pyridine ring and may be one or plural halogen groups, and in the case of plural halogen groups, they may be identical to or different from each other.

In the above formula (V), $R^2$ and $R^3$ each are a hydrogen atom or a hydrocarbon group, and $R^2$ and $R^3$ may have been unified.

m of $Ar^m$ is any integer selected from 1 to 3.

The boronic acid ester (V) may be of one or more types.

$R^2$ and $R^3$ each are preferably a hydrogen atom or an alkyl group or they have been unified to form an alkylene group, in the case of the alkyl group, they each are more preferably a linear or branched alkyl group having a carbon number of 1 to 6 and in the case of the alkylene group, they each are more preferably a linear or branched alkylene group having a carbon number of 1 to 12 and particularly preferably an ethylene group (dimethylene group) or a trimethylene group.

Conditions for the reaction between the halogenated quinoline represented by the aforementioned formula (IV) and the boronic acid ester represented by the aforementioned formula (V) are not particularly limited and can be set suitably with reference to, for example, conditions for known similar reactions. The ratio in amount (molar ratio) between the halogenated quinoline (IV) and boronic acid ester (V) is not particularly limited and is, for example, 1:2 to 1:10, preferably 1:2 to 1:4, and particularly preferably 1:2. Furthermore, for example, a reactant or solvent other than the halogenated quinoline (IV) and boronic acid ester (V) may or may not be used suitably as required. When a solvent is used, the concentration of the halogenated quinoline (IV) is not particularly limited and is, for example, 0.2 to 2.0 mol/L, preferably 0.3 to 1.5 mol/L, and more preferably 0.5 to 1.0 mol/L. A reactant to be used other than the halogenated quinoline (IV) and boronic acid ester (V) may be, for example, a catalyst. Examples of the catalyst include a palladium catalyst. The palladium catalyst is not particularly limited but, for example, Pd(PPh$_3$)$_4$ and Pd(PPh$_3$)$_2$Cl$_2$ are particularly preferable. Moreover, these catalysts may be used independently or two or more of them may be used in combination as required. The amount of the catalyst to be used is not particularly limited and is, for example, 0.002 to 0.1 time, preferably 0.005 to 0.04 time, and more preferably 0.01 to 0.02 time with respect to the number of moles of the halogenated quinoline (IV). These catalysts may or may not be used with another substance in combination as required. The aforementioned another substance is not particularly limited. Examples thereof include basic substances such as alkali metal carbonate, alkaline earth metal carbonate, and triethylamine, and, for example, K$_2$CO$_3$ and triethylamine are particularly preferable. The amounts of these to be used are not particularly limited and are, for example, 50 to 500 times, preferably 100 to 400 times, and more preferably 200 to 300 times with respect to the number of moles of the halogenated quinoline (IV). Furthermore, the solvent to be used for the reaction between the compounds (IV) and (V) is not particularly limited and may be, for example, water or an organic solvent. Examples of the organic solvent include ethers such as diethyl ether, tetrahydrofuran (THF), 1,3-dioxane, 1,4-dioxane, 1,3-dioxolane, thioxane, ethylene glycol dimethyl ether (1,2-dimethoxyethane), diethylene glycol dimethyl ether, and methyl-t-butyl ether as well as dichloroethane and DMF. These solvents may be used independently or two or more of them may be used in combination. The reaction temperature is not particularly limited and is, for example, 50 to 120° C., preferably 80 to 100° C., and more preferably 90 to 100° C. The reaction time also is not particularly limited and is, for example, 10 to 50 hours, preferably 15 to 30 hours, and more preferably 20 to 25 hours.

In a second process for producing a quinoline derivative represented by the aforementioned formula (II), it is preferable that it be produced by reacting 1-acyl-2-aminobenzene represented by the following formula (VI) with ketone represented by the following formula (VII).

[Chemical Formula 16]

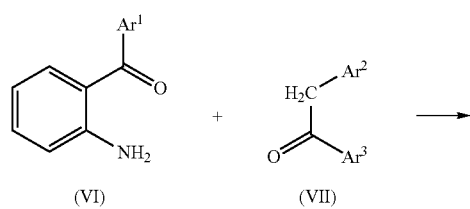

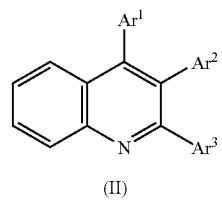

In the aforementioned formula (VI), Ar$^1$ is the same as that of the aforementioned formula (I). In the aforementioned formula (VII), Ar$^2$ and Ar$^3$ are the same as those of the aforementioned formula (I).

Conditions for the reaction between 1-acyl-2-aminobenzene represented by the aforementioned formula (VI) and ketone represented by the aforementioned formula (VII) are not particularly limited and can be set suitably with reference to, for example, conditions for known similar reactions. The ratio in amount (molar ratio) between 1-acyl-2-aminobenzene (VI) and ketone (VII) is not particularly limited and is, for example, 1:3 to 1:10, preferably 1:3 to 1:5, and particularly preferably 1:3. Furthermore, for example, a reactant or solvent other than 1-acyl-2-aminobenzene (VI) and ketone (VII) may or may not be used suitably as required. When a solvent is used, the concentration of 1-acyl-2-aminobenzene (VI) is not particularly limited and is, for example, 0.2 to 3.0 mol/L, preferably 0.5 to 2.0 mol/L, and more preferably 0.8 to 1.0 mol/L. Examples of the reactant other than 1-acyl-2-aminobenzene (VI) and ketone (VII) include phosphite such as diphenylphosphite, potassium hydroxide, and sodium hydroxide, and they may be used independently or two or more of them may be used in combination as required. The amounts of them to be used are not particularly limited and are, for example, 2 to 10 times, preferably 3 to 8 times, and more preferably 5 to 6 times with respect to the number of moles of 1-acyl-2-aminobenzene (VI). Furthermore, the solvent to be used for the reaction between 1-acyl-2-aminobenzene (VI) and ketone (VII) is not particularly limited and may be, for example, water or an organic solvent. The organic solvent is not particularly limited but is preferably a polar solvent. Examples thereof include phenols such as hydroxybenzene, orthocresol, metacresol, and paracresol, as well as DMF and DMSO. These solvents may be used independently or two or more of them may be used in combination. The reaction temperature is not particularly limited and is, for example, 100 to 200° C., preferably 120 to 160° C., and more preferably 130 to 140° C. The reaction time also is not particularly limited and is, for example, 5 to 30 hours, preferably 10 to 25 hours, and more preferably 20 to 25 hours.

The process for producing a compound represented by the aforementioned formula (VI) also is not particularly limited but it is preferable that it be produced by reacting, for example, a compound represented by the following formula (VIII) with a halide represented by the following formula (IX).

[Chemical Formula 17]

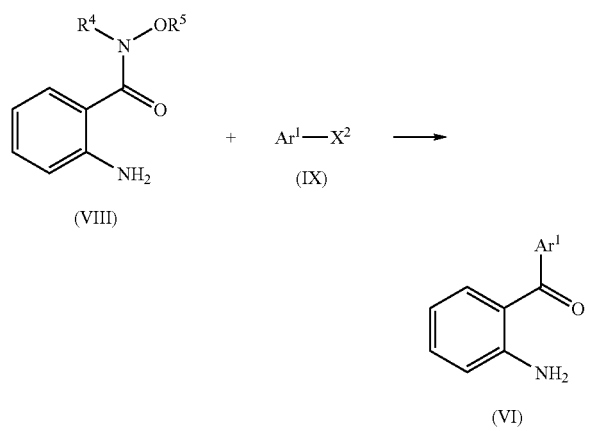

In the aforementioned formula (VIII), $R^4$ and $R^5$ each are a hydrogen atom or an alkyl group and they may be identical to or different from each other. In the aforementioned formula (IX), $Ar^1$ is the same as that of the aforementioned formula (VI) and $X^2$ is a halogen. $R^4$ and $R^5$ each are preferably a hydrogen atom or a linear or branched alkyl group having a carbon number of 1 to 6, and the alkyl group is particularly preferably a methyl group or an ethyl group.

Conditions for the reaction between a compound represented by the aforementioned formula (VIII) and a halide represented by the aforementioned formula (IX) are not particularly limited and can be set suitably with reference to, for example, conditions for known similar reactions. The ratio in amount (molar ratio) between the compound (VIII) and the halide (IX) is not particularly limited and is, for example, 1:1 to 1:2, preferably 1:1 to 1:1.5, and particularly preferably 1:1. Furthermore, for example, a reactant or solvent other than the compound (VIII) and halide (IX) may or may not be used suitably as required. When a solvent is used, the concentration of the compound (VIII) is not particularly limited and is, for example, 0.05 to 0.8 mol/L, preferably 0.1 to 0.5 mol/L, and more preferably 0.2 to 0.3 mol/L. Examples of the reactant other than the compound (VIII) and halide (IX) include organolithium reagents such as n-butyllithium, and they may be used independently or two or more of them may be used in combination as required. The amount of the organolithium reagent to be used is not particularly limited and is, for example, 1.5 to 2.5 times, preferably 1.6 to 2.3 times, and more preferably 1.9 to 2.1 times with respect to the number of moles of the compound (VIII). Furthermore, the solvent is not particularly limited and may be, for example, water or an organic solvent. Examples of the organic solvent include ethers such as diethyl ether, tetrahydrofuran (THF), 1,3-dioxane, 1,4-dioxane, 1,3-dioxolane, thioxane, ethylene glycol dimethyl ether (1,2-dimethoxyethane), diethylene glycol dimethyl ether, and methyl-t-butyl ether. These solvents may be used independently or two or more of them may be used in combination. The reaction temperature is not particularly limited and is, for example, minus 100 to minus 50° C., preferably minus 80 to minus 60° C., and more preferably minus 80 to minus 70° C. The reaction time also is not particularly limited and is, for example, 1 to 5 hours, preferably 2 to 4 hours, and more preferably 2 to 3 hours.

In the above, the production process of the present invention was described. Although, for example, the reactant and solvent to be used for the above-mentioned reactions are not particularly limited as described above, it is preferable that they be used in suitable combination. For instance, since a substance such as n-butyllithium has high reactivity with water, water in the solvent may affect the reactivity in some cases. In such cases, it is preferable that the solvent be used after as much water is removed therefrom as possible. Furthermore, as described above, the process for producing a compound of the present invention is not limited to those described above and can be any production process.

[Product, Reduction Method, and Oxidation Method of the Present Invention]

Next, the products, reduction methods, and oxidation methods of the present invention are described.

As described above, a compound (I') is used in each of products, reduction methods, and oxidation methods of the present invention. In the aforementioned formula (I'), $R^{100}$ is a hydrogen atom or an arbitrary substituent and is preferably, for example, a hydrogen atom, an alkyl group, a benzyl group, a carboxyalkyl group (alkyl group with a carboxyl group added to the end thereof), an aminoalkyl group (alkyl group with an amino group added to the end thereof), or a polyether chain. Furthermore, the compound (I') is more preferably a compound of the present invention, i.e. a new compound (a quinolinium ion derivative represented by the aforementioned formula (I), a stereoisomer or tautomer thereof, or a salt thereof) that the present inventors invented.

As described above, the compound (I') can provide a charge-separated state with longevity and not only high oxidizing power but also high reducing power. The products of the present invention, i.e. photocatalysts, photosensitizers, dyes, oxidants, reductants, cells, dye-sensitized solar cells, and organic EL devices of the present invention can exhibit their excellent functions through generation of the charge-separated state. That is, the compound (I') allows electron transfer to occur between molecules represented by the aforementioned formula (I') or between a molecule of the aforementioned formula (I') and another substance through, for example, generation of the aforementioned charge-separated state. This allows the compound (I') to be used suitably for applications relating to electron transfer that occurs between the aforementioned molecules or substances, that is, for example, the aforementioned oxidants, reductants, and cells. Particularly, since the compound (I') has excellent reducing power, it can be used suitably for reductants as described above. For instance, it is possible to transfer electrons from a charge-separated state of the compound (I') to an electron acceptor substance such as viologen and thereby perform an electron transfer reduction reaction. Furthermore, the substances that the reductants of the present invention can reduce (substances to be reduced) are not limited to electron acceptor substances such as the above-mentioned viologen. The reductants of the present invention can be used for reduction reactions of various substances. The substances to be reduced are not particularly limited. Examples thereof include quinones, nitrobenzenes, and cyanobenzenes.

Moreover, the organic EL devices of the present invention are, for example, as follows. First, in an example of the structure of a common organic EL device, a transparent electrode (anode), an organic light-emitting layer, and a metal electrode (cathode) are stacked on a transparent substrate in this order. The organic light-emitting layer contains a light-emitting material. In such an organic EL device, voltage is applied to the anode and the cathode to inject positive holes and electrons into the organic light-emitting layer. Energy produced through recombination of the positive holes with electrons excites the light-emitting material. The light-emitting material thus excited then emits light when returning to the ground state. The organic EL devices of the present invention may be those, that contain a compound (I') as the light-emitting material. With this configuration, for example, a charge-separated state is generated through excitation of the compound (I') and further light is emitted when it returns from the excited state (charge-separated state) to the ground state. The organic EL devices of the present invention are not limited by this description by any means.

The method of generating the charge-separated state of the compound (I') is not particularly limited and is preferably, for example, photoexcitation and particularly preferably visible light excitation due to its further simplicity. In order to perform visible light excitation, as described above, it is preferable that the compound (I') have an absorption band in a visible region. This also makes it possible easily to generate a charge-separated state with longevity as well as both high oxidizing power and high reducing power.

The compound (I') can be used, for example, for photocatalysts and photosensitizers by allowing the charge-separated state to be generated through photoexcitation and electron transfer to occur between the molecules or substances as described above. For example, as described above, when the compound (I') is combined with a platinum catalyst, it also is possible to obtain a hydrogen-evolving photocatalyst. Furthermore, the compound (I') can be used as a dye having an absorption band in a visible region. For instance, as described above, the cells of the present invention also can be used as dye-sensitized solar cells when containing the compound (I') as a dye.

The method for photoexciting the compound (I') is not particularly limited. For instance, the compound (I') may be dissolved in a solvent to be a solution and thereafter this may be photoirradiated. The solvent is not particularly limited and may be, for example, water or an organic solvent. Examples of the organic solvent include nitrites such as benzonitrile, acetonitrile, and butyronitrile, halogenated solvents such as chloroform and dichloromethane, ethers such as tetrahydrofuran (THF), amides such as dimethylformamide (DMF), sulfoxides such as dimethyl sulfoxide (DMSO), ketones such as acetone, and alcohols such as methanol. These solvents may be used independently or two or more of them may be used in combination. The solvent is preferably a high polarity solvent from the viewpoints of, for example, solubility of the compound (I') and stability of the excited state and is particularly preferably acetonitrile from the viewpoint of, for example, the solubility.

In the aforementioned solution, the concentration of the compound (I') is not particularly limited and may be adjusted suitably as required, but it is adjusted so that the concentration of the quinolinium ion derivative represented by the aforementioned formula (I') is, for example, at least $5 \times 10^{-5}$ M and preferably $1 \times 10^{-4}$ to $1 \times 10^{-3}$ M.

Furthermore, the excitation light also is not particularly limited but is preferably, for example, visible light. Particularly, the use of visible light contained in natural light such as sunlight allows excitation to be performed easily. Among the wavelengths of the visible light used for irradiation, a more preferred wavelength depends on the absorption band of the compound (I'), but when the quinolinium ion derivative is represented by any one of the aforementioned formulae 1 to 5, the wavelength is, for example, more preferably 300 to 450 nm and further preferably 300 to 360 nm. The temperature to be employed for irradiation with visible light also is not particularly limited. For instance, when the quinolinium ion derivative is represented by any one of the aforementioned formulae 1 to 5, it also is possible to allow the reaction (excitation) to progress at a room temperature of about 10 to 30° C.

Furthermore, as described above, the reduction method of the present invention includes producing an excited species in an electron-transfer state (charge-separated state) by exciting the compound (I') through photoirradiation and reducing the substance to be reduced by transferring electrons from the excited species to the substance to be reduced. Similarly, the oxidation method of the present invention includes producing an excited species in an electron-transfer state (charge-separated state) by exciting the compound (I') through photoirradiation and reducing the substance to be oxidized by transferring electrons from the substance to be oxidized to the excited species. That is, the compound (I') also can be used as a reductant or an oxidant in the aforementioned reduction or oxidation method of the present invention, in which photoexcitation is utilized.

Specific methods for performing the reduction or oxidation method of the present invention are not particularly limited. For instance, the step of producing the excited species through photoirradiation may be performed through photoirradiation after the compound (I') is dissolved in a solvent to form a solution, as described above. Furthermore, it may be performed through photoirradiation after the compound (I') is dissolved in a solvent together with the substance to be reduced or the substance to be oxidized to form a mixed solution. In these cases, various conditions such as the solvent, solution concentration, irradiation light wavelength, and temperature to be employed are not particularly limited and are, for example, as described above. The aforementioned reduction or oxidization step also is not particularly limited. For example, in the reduction method of the present invention, the aforementioned reduction step may be one in which after photoirradiation of the mixed solution, electron transfer occurs automatically from the excited species to the substance to be reduced. Similarly, in the oxidation method of the present invention, the aforementioned reduction step may be one in which after photoirradiation of the mixed solution, electron transfer occurs automatically from the substance to be oxidized to the excited species.

In the reduction method of the present invention, the substance to be reduced is not particularly limited. Examples thereof include quinones, nitrobenzenes, and cyanobenzenes. The ratio in amount (molar ratio) between the molecule represented by the aforementioned formula (I') and the substance to be reduced is not particularly limited and can be selected suitably according to, for example, the types of the molecule represented by the aforementioned formula (I') and the substance to be reduced. The ratio in amount is, for example, 1:0.001 to 1:1000, preferably 1:0.005 to 1:100, more preferably 1:0.01 to 1:10, and particularly preferably 1:0.1 to 1:1.

In the oxidation method of the present invention, the substance to be oxidized is not particularly limited and examples thereof include alkyl benzenes, alkyl naphthalenes, alkyl anthracenes, and NADH analogs. The ratio in amount (molar ratio) between the molecule represented by the aforementioned formula (I') and the substance to be oxidized is not particularly limited and can be selected suitably according to, for example, the types of the molecule represented by the aforementioned formula (I') and the substance to be oxidized. The ratio in amount is, for example, 1:0.001 to 1:1000, preferably 1:0.005 to 1:100, more preferably 1:0.01 to 1:10, and particularly preferably 1:0.1 to 1:1.

Furthermore, the applications and the methods for use of the compounds of the present invention among the compounds (I'), that is, new compounds (quinolinium ion derivatives represented by the aforementioned formula (I), stereoisomers or tautomers thereof, or salts thereof) according to the invention made by the present inventors are not limited to the above descriptions. Any applications and methods for use can be employed.

EXAMPLES

Next, examples of the present invention are described but the present invention is not limited to the following examples. The theoretical speculations about, for example, reaction mechanisms described in the following examples merely indicate examples of, for instance, presumable mechanisms and do not limit the present invention by any means.

In the following examples, the nuclear magnetic resonance (NMR) spectrum was measured using an apparatus, JNM-AL300 NMR spectrometer (trade name) (300 MHz for $^1$H measurement), manufactured by JEOL Ltd. The chemical shift is indicated in parts per million (ppm). Tetramethylsilane (TMS) was used for the internal standard, 0 ppm. The coupling constant (J) is indicated in hertz, and the brevity codes s, d, t, q, m and br indicate singlet, doublet, triplet, quartet, multiplet, and broad, respectively. The mass spectrometry (MS) was measured by the MALDI-TOF-MS method using an apparatus, Kratos Compact MALDI I (trade name), manufactured by Shimadzu Corporation. The element analysis value was measured using Model 240C (trade name) manufactured by Perkin-Elmer. The voltammetry was measured using an apparatus, ALS630B electrochemical analyzer (trade name), manufactured by BAS Inc. The absorbance was measured using an apparatus, 8453 photodiode array spectrophotometer (trade name), manufactured by Hewlett-Packard. An apparatus, Nd:YAG laser (SLII-10, 4-6 ns fwhm) (trade name), manufactured by Continuum, Inc., was used for laser irradiation. All the chemicals were of reagent grade and were purchased from Tokyo Chemical Industry Co., Ltd., Wako Pure Chemical Industries, Ltd., and Aldrich.

Examples 1 to 5

As described below, salts of quinolinium ion derivatives represented by the aforementioned formulae 1 to 5 were synthesized (Examples 1 to 5, respectively), and the properties such as the oxidation-reduction potential and generation of a charge-separated state through photoexcitation were checked.

[1] Synthesis of Quinolinium Ion Derivatives 1 to 5

Salts of the quinolinium derivatives represented by the aforementioned formulae 1 to 5 were synthesized. The aforementioned formulae 1 to 5 will be indicated below once again.

[Chemical Formula 18]

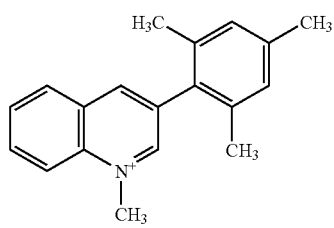

1

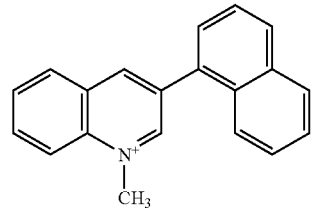

2

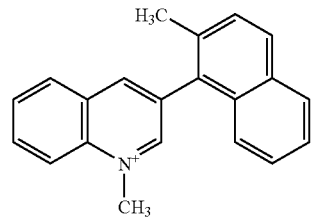

3

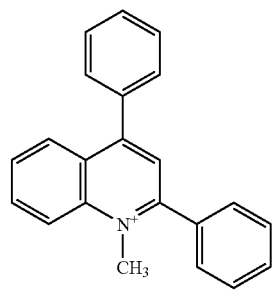

4

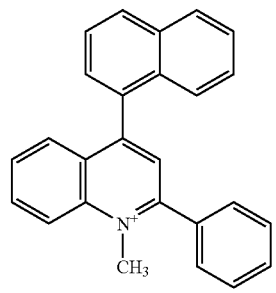

5

[1-1] Synthesis of Quinolinium Ion Derivatives 1 to 3 (Examples 1 to 3)

Perchlorate of quinolinium ion derivative 2 (3-(1-naphthyl)quinolinium ion) was synthesized according to the following scheme 1.

Scheme 1

[Chemical Formula 19]

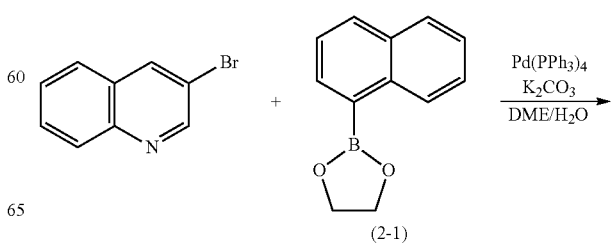

(2-1)

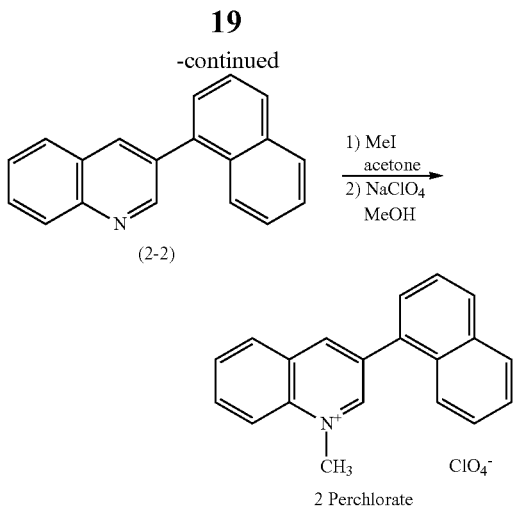

Hereinafter, the above-mentioned scheme 1 is described in further detail.

Before the reaction of the above-mentioned scheme 1 was performed, 1-naphthylboronic acid ester (2-1) was synthesized first. That is, first, a Grignard reagent was produced in 10 mL of dehydrated THF through the reaction between 1-naphthyl bromide (2.07 g, 10.0 mmol) and magnesium (0.27 g, 11.0 mmol). Subsequently, this Grignard reagent was added to 10 mL of dehydrated THF solution of trimethoxyborane (2.08 g, 20.0 mmol) at −78° C., which then was stirred for one hour. After completion of the reaction, the solvent was removed therefrom, and the resultant white solid was placed in 50 mL of toluene and 5 mL of ethylene glycol was added thereto under stirring. Thereafter, it was refluxed at 115° C. for 12 hours to be reacted. After completion of the reaction, it was cooled to room temperature and only the toluene phase was extracted and thus the solvent was removed. As a result, 1-naphthylboronic acid ester (2-1) was obtained (1.60 g, 81%). The instrumental analysis data of the 1-naphthylboronic acid ester (2-1) is indicated below.

1-naphthylboronic acid ester (2-1)

$^1$H NMR (300 MHz, CDCl$_3$) δ 8.73 (d, J=7.5 Hz, 1H), 8.11 (s, J=7.5 Hz, 1H), 7.95 (s, J=7.5 Hz, 1H), 7.84 (s, J=7.5 Hz, 1H), 7.56-7.45 (m, 3H), 4.52 (s, 4H).

Next, 1.0 mL of 2.0 M potassium carbonate aqueous solution and tris(triphenylphosphine)palladium [Pd(PPh$_3$)$_4$] (30 mg, 0.026 mmol) were added to 4 mL of dimethoxyethane (DME) solution of the 1-naphthylboronic acid ester (2-1) (1.00 g, 5.00 mmol) and 3-bromoquinoline (0.62 g, 3.00 mmol), which then was refluxed at 90° C. for 12 hours. After completion of the reaction, it was cooled to room temperature, and 100 mL of chloroform was added thereto. This was washed with 100 mL of water twice and subsequently was washed with 50 mL of saturated saline. The solvent was removed therefrom and this then was purified by column chromatography using chloroform as a developing solvent. Thus 3-(1-naphthyl)quinoline (2-2) was obtained (84 mg, 11%). The instrumental analysis data of this 3-(1-naphthyl)quinoline (2-2) is indicated below.

3-(1-naphthyl)quinoline (2-2)

$^1$H NMR (300 MHz, CDCl$_3$) δ 9.06 (s, 1H), 8.28 (s, 1H), 8.21 (d, J=8.4 Hz, 1H), 7.97-7.75 (m, 5H), 7.65-7.46 (m, 5H).

Furthermore, the 3-(1-naphthyl)quinoline (2-2) (70 mg, 0.27 mmol) was dissolved in 10 ml of acetone, and further methyl iodide (130 μl, 2 mmol) was added thereto, which then was stirred for 10 hours. The solvent was removed therefrom and 20 mL of methanol was then added thereto. Subsequently, sodium perchlorate (0.12 g, 1.0 mmol) was added thereto and thereby salt exchange (ion exchange) was performed. Thus, perchlorate of 3-(1-naphthyl)quinolinium ion (quinolinium ion derivative 2) was obtained. The yield amount of the quinolinium ion derivative 2 perchlorate thus obtained was 93 mg and the yield from the 3-(1-naphthyl)quinoline (2-2) was 93%. The instrumental analysis data of this quinolinium ion derivative 2 perchlorate is indicated below.

Quinolinium ion derivative 2 perchlorate $^1$H NMR (300 MHz, CD$_3$CN) δ 9.25 (s, 1H), 9.20 (s, 1H), 8.42 (t, J=8.4 Hz, 2H), 8.30 (t, J=8.4 Hz, 1H), 8.15-8.08 (m, 3H), 7.86 (d, J=8.4 Hz, 1H), 7.74-7.56 (m, 4H), 4.63 (s, 3H), MALDI-TOF-MS m/z 270 (M$^+$ Calcd for C$_{20}$H$_{16}$N 270.1). Anal. Calcd for C$_{20}$H$_{16}$ClNO$_4$: C, 64.96; H, 4.36; N, 3.79. Found: C, 64.80; H, 4.24; N, 3.82.

Furthermore, perchlorate of the quinolinium ion derivative 1 was obtained in the same manner as in the above-mentioned scheme 1 except that mesityl bromide was used instead of 1-naphthyl bromide. Furthermore, perchlorate of the quinolinium ion derivative 3 was obtained in the same manner as in the above-mentioned scheme 1 except that 2-methyl1-naphthyl bromide was used instead of 1-naphthyl bromide. The instrumental analysis data of these quinolinium ion derivative 1 perchlorate, quinolinium ion derivative 3 perchlorate, and intermediates thereof are indicated below.

3-(1-mesityl)quinoline (intermediate of quinolinium ion derivative 1 perchlorate)

$^1$ H NMR (300 MHz, CDCl$_3$) δ 8.67 (s, 1H), 8.14 (d, J=8.4 Hz, 1H), 7.96 (s, 1H), 7.76-7.55 (m, 3H), 7.00 (s, 2H), 2.34 (s, 3H), 2.03 (s, 6H).

3-[1-(2-methyl)naphthyl)]quinoline (intermediate of quinolinium ion derivative 3 perchlorate)

$^1$H NMR (300 MHz, CDCl$_3$) δ 8.85 (s, 1H), 8.22 (d, J=8.4 Hz, 1H), 8.10 (s, 1H), 7.89-7.60 (m, 6H), 7.49-7.32 (m, 3H), 2.29 (s, 3H).

Quinolinium ion derivative 1 perchlorate $^1$H NMR (300 MHz, CD$_3$CN) δ 8.93 (s, 1H), 8.90 (s, 1H), 8.39 (d, J=7.8 Hz, 1H), 8.33 (d, J=7.8 Hz, 1H), 8.26 (t, J=7.8 Hz, 1H), 8.04 (t, J=7.8 Hz, 1H), 7.08 (s, 2H), 2.04 (s, 6H), 4.57 (s, 3H), 2.35 (s, 3H), MALDI-TOF-MS m/z 262 (M$^+$ Calcd for C$_{19}$H$_{20}$N 261.8). Anal. Calcd for C$_{19}$H$_{20}$ClNO$_4$: C, 63.07; H, 5.57; N, 3.87. Found: C, 62.91; H, 5.49; N, 3.89.

Quinolinium ion derivative 3 perchlorate $^1$H NMR (300 MHz, CD$_3$CN) δ 9.09 (s, 1H), 9.05 (s, 1H), 8.49-8.25 (m, 3H), 7.96-8.12 (m, 3H), 7.62-7.32 (m, 4H), 4.61 (s, 3H), 2.38 (s, 3H), MALDI-TOF-MS m/z 284 (M$^+$ Calcd for C$_{21}$H$_{18}$N 284.1). Anal. Calcd for C$_{21}$H$_{18}$ClNO$_4$: C, 65.71; H, 4.73; N, 3.65. Found: C, 65.58; H, 4.73; N, 3.65.

[1-2] Synthesis of Quinolinium Ion Derivatives 4 and 5 (Examples 4 and 5)

According to the following scheme 2, perchlorate of quinolinium ion derivative 5 (2-phenyl-4-(1-naphthyl)quinolinium ion) was synthesized.

Scheme 2

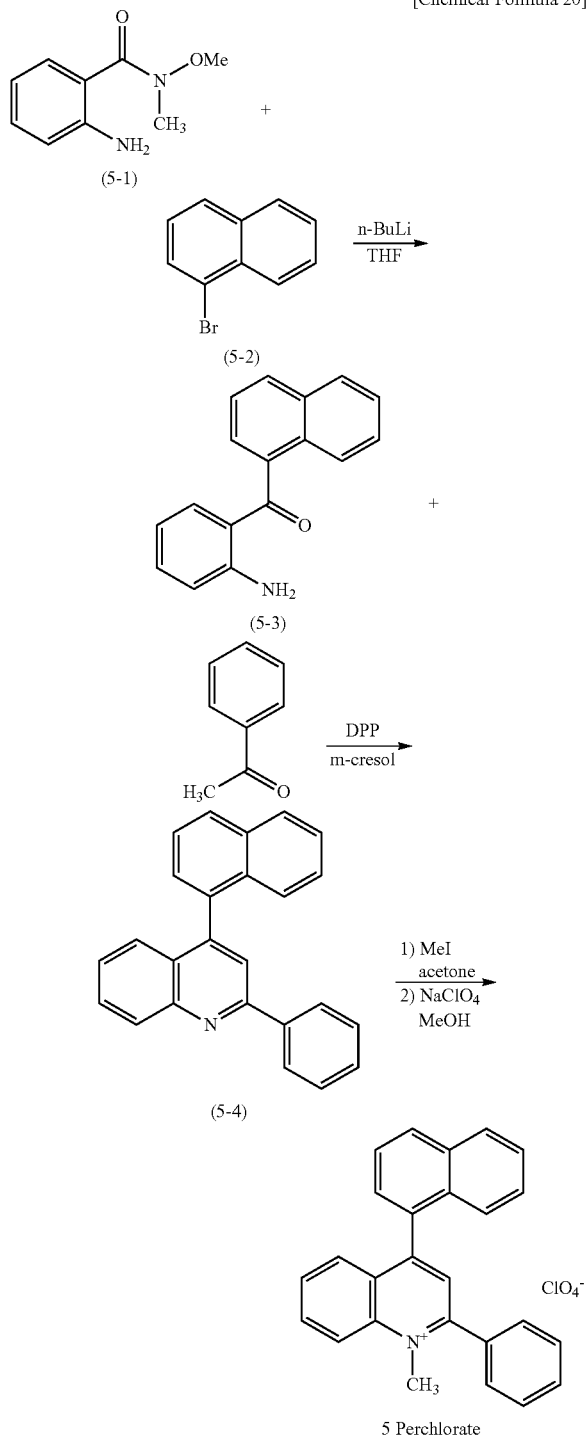

The reaction of the above-mentioned scheme 2 was performed specifically as follows. That is, first, anthranilic acid N-methoxy-N-methylamide (5-1) (2.00 g, 11.1 mmol) and 1-naphthyl bromide (5-2) (2.29 g, 11.1 mmol) were dissolved in 60 mL of dehydrated THF. Next, this solution was cooled to −78° C., and while this temperature was maintained, an n-butyllithium hexane solution (13.8 mL, 1.6 M, and 22.2 mmol) was dropped thereinto over 20 minutes with stirring. After dropping, 20 mL of 1N hydrochloric acid was added thereto and extraction was performed with 150 mL of ethyl acetate. This was washed with 100 mL of water twice and subsequently was washed with 50 mL of saturated saline. The organic solvent was removed therefrom and this was then purified by column chromatography using chloroform as a developing solvent. Thus 1'-naphthyl-2-aminobenzophenone (5-3) was obtained. The yield amount was 500 mg, and the yield was 18%. The instrumental analysis data of this 1'-naphthyl-2-aminobenzophenone (5-3) is indicated below.

1'-naphthyl-2-aminobenzophenone (5-3)

$^1$H NMR (300 MHz, CDCl$_3$) δ 7.97-7.93 (m, 3H), 7.49-7.42 (m, 4H), 7.28-7.20 (m, 2H), 6.73 (d, J=7.5 Hz, 1H), 6.52 (bs, 1H), 6.43 (t, J=7.5 Hz, 3H).

Next, diphenylphosphite (DPP) (2.5 g, 10.0 mmol) and m-cresol (1.6 g, 14.8 mmol) were added to 1'-naphthyl-2-aminobenzophenone (5-3) (400 mg, 1.6 mmol) and acetophenone (400 mg, 4.4 mmol). This then was stirred at 140° C. for five hours. After completion of the reaction, it was cooled to room temperature. Thereafter, 100 mL of 10% sodium hydroxide solution and 100 mL of methylene chloride were added thereto. Methylene chloride was separated to be recovered and then was washed with 100 mL of water three times. Subsequently, this was washed with 50 mL of saturated saline. The solvent was removed therefrom and this was then purified by column chromatography using chloroform as a developing solvent. Thus, 2-phenyl-4-(1-naphthyl)quinoline (5-4) was obtained. The yield amount was 150 mg, and the yield from 1'-naphthyl-2-aminobenzophenone (5-3) was 28%. The instrumental analysis data of this 2-phenyl-4-(1-naphthyl)quinoline (5-4) is indicated below.

2-phenyl-4-(1-naphthyl)quinoline (5-4)

$^1$H NMR (300 MHz, CDCl$_3$) δ 8.27 (d, J=8.5 Hz, 1H), 8.21 (d, J=8.5 Hz, 2H), 7.97 (t, J=8.5 Hz, 2H), 7.91 s, 1H), 7.71 (t, J=8.5 Hz, 1H), 7.61-7.32 (m, 11H).

Furthermore, methyl triflate (methyl trifluoromethanesulfonate) (82 mg, 0.50 mmol) was added to 10 mL of methylene chloride solution of 4-naphthyl-2-phenylquinoline (5-4) (150 mg, 0.45 mmol), which then was stirred at room temperature for two hours. The solvent was removed therefrom and 20 mL of methanol was added thereto. Sodium perchlorate (0.12 g, 1.0 mmol) was then added thereto and thereby salt exchange was performed to obtain perchlorate. Recrystallization was performed using hot methanol and thereby 190 mg of perchlorate of 2-phenyl-4-(1-naphthyl)quinolinium ion (quinolinium ion derivative 5) was obtained. The yield from 4-naphthyl-2-phenylquinoline (5-4) was 95%. The instrumental analysis data of the quinolinium ion derivative 5 perchlorate is indicated as follows.

Quinolinium ion derivative 5 perchlorate $^1$H NMR (300 MHz, CD$_3$CN) δ 8.52 (d, J=9.0 Hz, 1H), 8.25 (t, J=9.0 Hz, 1H), 8.18 (d, J=9.0 Hz, 1H), 8.08 (d, J=9.0 Hz, 1H), 8.05 (s, 1H), 7.82-7.69 (m, 8H), 7.61 (t, J=9.0 Hz, 2H), 7.45 (t, J=9.0 Hz, 1H), 7.41 (d, J=9.0 Hz, 1H), 4.44 (s, 3H), MALDI-TOF-MS m/z 346 (M$^+$ Calcd for C$_{20}$H$_{16}$N 346.2). Anal. Calcd for C$_{26}$H$_{20}$ClNO$_4$: C, 70.03; H, 4.52; N, 3.14. Found: C, 69.78; H, 4.39; N, 3.19.

Furthermore, perchlorate of quinolinium ion derivative 4 was obtained in the same manner as in the above-mentioned scheme 2 except that bromobenzene was used instead of 1-naphthyl bromide. The instrumental analysis data of the quinolinium ion derivative 4 perchlorate and the intermediate thereof were indicated below.

2,4-diphenylquinoline (intermediate of quinolinium ion derivative 4 perchlorate)

$^1$H NMR (300 MHz, CDCl$_3$) δ 8.26-8.18 (m, 2H), 7.90 (d, J=8.4 Hz, 1H), 7.82 (s, 1H), 7.73 (t, J=8.4 Hz, 1H), 7.57-7.43 (m, 10H).

Quinolinium ion derivative 4 perchlorate $^1$H NMR (300 MHz, CD$_3$CN) δ 8.48 (d, J=8.4 Hz, 1H), 8.31-8.25 (m, 2H), 7.98 (t, J=8.4 Hz, 1H), 7.95 (s, 1H), 7.75-7.67 (m, 10H), 4.36 (s, 3H), MALDI-TOF-MS m/z 270 (M$^+$ Calcd for C$_{20}$H$_{16}$N 270.1). Anal. Calcd for C$_{22}$H$_{18}$ClNO$_4$: C, 66.75; H, 4.58; N, 3.54.

[2] Voltammetry

Using respective perchlorates of quinolinium ion derivatives 1 to 5 synthesized as described above (compounds of Examples 1 to 5), with respect to each of the quinolinium ion derivatives, oxidation-reduction potentials were measured by the cyclic voltammetric method and second harmonic voltammetric method. FIG. 1 shows reduction waves (cyclic voltammogram) of the quinolinium ion derivative 5, i.e. 2-phenyl-4-(1-naphthyl)quinolinium ion (2.0 mM), measured in an acetonitrile solution containing 0.1 M tetrabutylammonium perchlorate. It was proved from the reduction waves shown in FIG. 1 that the reduction potential of 2-phenyl-4-(1-naphthyl)quinolinium ion (quinolinium ion derivative 5) was very low, specifically, −0.90 V vs SCE. This suggests that the quinolinium ion derivative 5 has strong reducing power. Furthermore, the oxidation potential of the quinolinium ion derivative 5 was measured by the second harmonic voltammetric method and was found to be 1.87 V vs SCE. That is, it was proved that the energy of the electron-transfer state (charge-separated state) of the quinolinium ion derivative 5 was very high, specifically 2.77 eV.

Furthermore, with respect to the quinolinium ion derivatives 1 to 4, it was proved by the same measurement that the reduction potential was low and the energy of the electron-transfer state (charge-separated state) was high. For instance, according to the cyclic voltammetry, the quinolinium ion derivative 2 had a reduction potential of −0.88 V vs SCE and the quinolinium ion derivative 4 had a reduction potential of −0.89 V vs SCE. Moreover, the oxidation potential of the quinolinium ion derivative 2 was measured by the second harmonic voltammetric method and thereby was found to be 1.82 V vs SCE. That is, it was proved that the energy of the electron-transfer state (charge-separated state) of the quinolinium ion derivative 2 was very high, specifically, 2.70 eV.

As described above, 9-mesityl-10-methylacridinium ion (see Nonpatent Documents 1 and 2) represented by the following formula (X) has been known conventionally and the reduction potential thereof was −0.49 V vs SCE. That is, it was proved that although the quinolinium ion derivative of this example had a similar structure to that of 9-mesityl-10-methylacridinium ion, the reduction potential to serve as an index that indicated reducing power was remarkably low. The fact that, as described above, the quinolinium ion derivative of this example has a very high energy of the electron-transfer state (charge-separated state) and a very low reduction potential indicates usefulness thereof as a reductant.

[Chemical Formula 21]

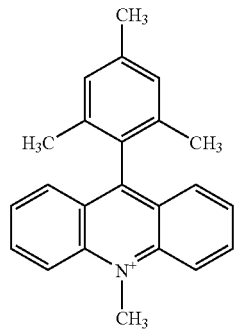

(X)

[Excitation]

When photoirradiation was performed with respect to a deoxygenated acetonitrile solution (0.1 mM) of 2-phenyl-4-(1-naphthyl)quinolinium ion (quinolinium ion derivative 5), the fluorescence intensity was reduced significantly as compared to quinolinium ions. Conceivably, such a reduction in fluorescence intensity results from photoinduced electron transfer from the singlet excited state of the quinolinium ion to naphthalene bound thereto. Furthermore, similarly with respect to other quinolinium ion derivatives, the same measurement was performed and as a result, a significant reduction in fluorescence intensity was observed.

Furthermore, femtosecond laser flash photolysis (laser time-resolved spectroscopy) was performed in acetonitrile with respect to 2-phenyl-4-(1-naphthyl)quinolinium ion (quinolinium ion derivative 5) and the transient absorption spectrum was then measured. As a result, occurrence of the photoinduced electron transfer was observed.

Figure 2:
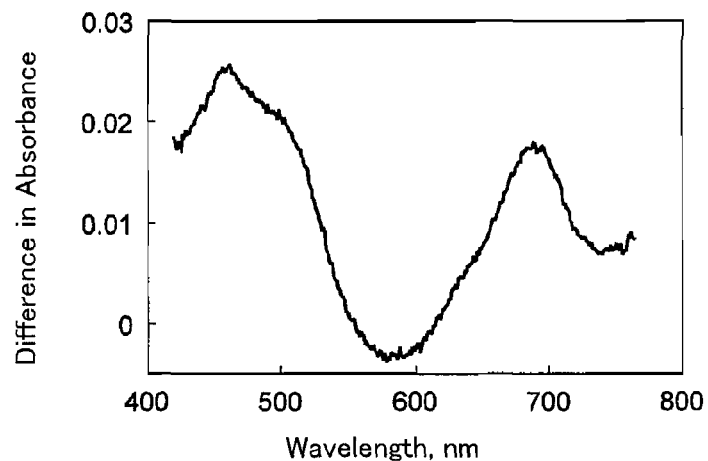
FIG. 2 is a diagram showing an example of the transient absorption spectrum in femtosecond laser flash photolysis (laser time-resolved spectroscopy) of a quinolinium ion derivative according to the present invention.

The femtosecond laser flash photolysis was carried out as follows. That is, the deoxygenated acetonitrile solution (0.1 mM) of 2-phenyl-4-(1-naphthyl)quinolinium ion (quinolinium ion derivative 5) perchlorate was irradiated with a femtosecond laser (390 nm) at 298 K (25° C.). A transient absorption spectrum was measured 10 ps after irradiation. FIG. 2 shows the transient absorption spectrum. As shown in FIG. 2, this transient absorption spectrum has one absorption band between 400 and 500 nm and further has another absorption band around 700 nm. That is, this transient absorption spectrum corresponds to superposition of the absorption band (420 nm) originating from the quinolinyl radical and the absorption band (700 nm) originating from the naphthalene radical cation in the acetonitrile. Accordingly, it is conceivable that this transient absorption spectrum indicates the occurrence of photoinduced electron transfer with respect to the quinolinium ion derivative 5. More specifically, it is surmised that photoirradiation to the quinolinium ion derivative 5 allowed the singlet excited state of the quinolinium ion site to be generated, electron transfer occurred from the singlet excited state to the naphthalene site bound thereto, and thereby an electron-transfer state was formed. However, these discussions do not limit the present invention.

Furthermore, the same femtosecond laser flash photolysis measurement also was carried out with respect to the quinolinium ion derivatives of Examples 1 to 4, and as a result, the same phenomena were observed. As described above, the quinolinium ion derivatives of Examples 1 to 5 each formed a good electron-transfer state (charge-separated state).

As described above, in Examples 1 to 5, quinolinium ion derivatives 1 to 5 were synthesized. These had excellent electron transfer properties as they were confirmed by the cyclic voltammetry and femtosecond laser flash photolysis. Specifically, the charge-separated states (electron-transfer states) of the quinolinium ion derivatives 1 to 5 each had high energy and longevity and had high reducing power and oxidizing power. These indicate that the quinolinium ion derivatives of Examples 1 to 5 are excellent electron donor-acceptor dyads (donor-acceptor dyads) that are useful for industrial applications using the charge-separated state, for example, various applications such as reductants, oxidants, and photocatalysts.

With respect to the quinolinium ion derivatives 2 and 5, electron orbital was calculated by the density functional theory (B3LYP/6-31G method). As a result, in each of them, the lowest unoccupied molecular orbit (LUMO) was localized in the quinoline ring portion and the highest occupied molecular orbit (HOMO) was localized in the naphthalene ring portion. Furthermore, the quinoline ring and the naphthalene ring were substantially orthogonal to each other. These theoretical calculation results suggest that with respect to the quinolinium ion derivatives 2 and 5, there is almost no orbital interaction (for instance, pi-coupling between a donor site and an acceptor site) in the charge-separated state that is generated through photoexcitation. Generally, in an electron donor-acceptor dyad (donor-acceptor dyad), the orbital interaction between the donor site and the acceptor site must be small. The compound of the present invention hardly causes this orbital interaction and therefore is considered to be excellent as a donor-acceptor linked-type molecule. However, this calculation result merely indicates one example of examinations that were made through the theoretical calculation and does not limit the present invention by any means.

Example 6

Reductant and Reduction Method

The quinolinium ion derivatives 1 to 5 synthesized in Examples 1 to 5 each were subjected to an electron transfer reaction (reduction reaction) from the electron-transfer state (charge-separated state) to the electron acceptor molecule, and thereby the reducing ability of the electron-transfer state (charge-separated state) was checked. The electron acceptor molecule (substance to be reduced) used herein was hexylviologen.

The electron transfer reaction (reduction reaction) is described below in further detail. That is, first, both the hexylviologen and perchlorate of the 2-phenyl-4-(1-naphthyl)quinolinium ion (quinolinium ion derivative 5) synthesized in Example 5 described above were dissolved in deoxygenated acetonitrile and thereby a mixed solution of 2-phenyl-4-(1-naphthyl)quinolinium ion and hexylviologen was obtained. The concentration of this mixed solution was set so that the 2-phenyl-4-(1-naphthyl)quinolinium ion concentration was 0.1 mM and the hexylviologen concentration was 1.0 mM. Subsequently, the mixed solution was irradiated with a laser beam having a wavelength of 355 nm at 298 K (25° C.), so that nanosecond laser excitation was performed. Thereafter, the transient absorption spectra were measured 1.2 and 20 microseconds after irradiation.

Figure 3:
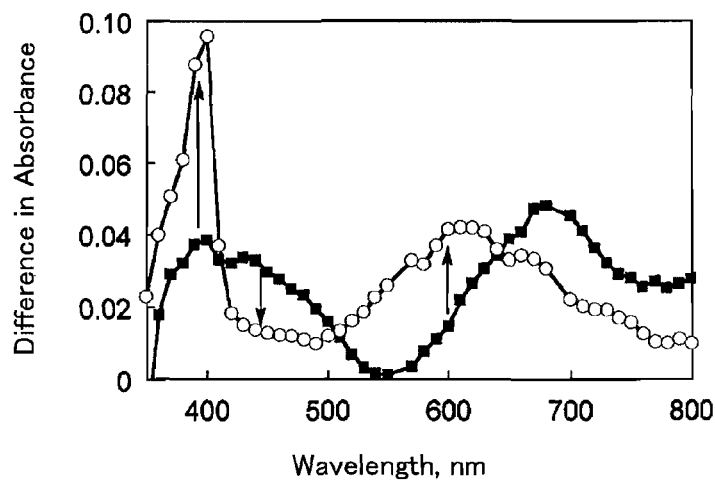
FIG. 3 is a diagram showing an example of the transient absorption spectrum in an electron transfer reaction from a quinolinium ion derivative of the present invention to hexylviologen.

FIG. 3 shows the transient absorption spectra thereof. In FIG. 3, "■" denotes the transient absorption spectrum measured 1.2 microseconds after irradiation while "○" denotes the transient absorption spectrum measured 20 microseconds after irradiation. As shown in FIG. 3, the absorption bands in the transient absorption spectrum ("■") measured 1.2 microseconds after irradiation coincided well with the absorption bands indicated in the spectrum shown in FIG. 2. According to these absorption bands, it is surmised that in the 2-phenyl-4-(1-naphthyl)quinolinium ion (quinolinium ion derivative 5), a similar electron-transfer state (charge-separated state) to that shown in FIG. 2 was formed through the nanosecond laser excitation. Furthermore, conceivably, it suggests that the electron-transfer state (charge-separated state) has longevity to such an extent that it is maintained even 1.2 microseconds after laser beam irradiation. Moreover, in the transient absorption spectrum ("○") measured 20 microseconds after irradiation, as shown in FIG. 3, the absorption band (420 nm) that seemed to originate from the quinolinyl radical was reduced while the absorption bands (390 nm and 600 nm) that seemed to originate from the hexylviologen radical cation appeared. This suggests that the electron transfer from the 2-phenyl-4-(1-naphthyl)quinolinium ion (quinolinium ion derivative 5) to hexylviologen, i.e. a reduction reaction occurred efficiently.

Furthermore, the same measurements also were carried out with respect to the quinolinium ion derivatives of Examples 1 to 4, and thereby similar phenomena were observed.

As described above, in this example, the quinolinium ion derivatives of Examples 1 to 5 were used for reductants of the present invention and thereby substances to be reduced were reduced. Furthermore, in this example, as described above, the quinolinium ion derivatives each were excited through photoirradiation performed with respect to the mixed solution of a quinolinium ion derivative and a substance to be reduced. Thereafter, the substance to be reduced was reduced through electron transfer from the excited species (charge-separated state) to the substance to be reduced. Accordingly, this example also is an example of the reduction method according to the present invention.

Example 7

Oxidant and Oxidation Method

A substance to be oxidized was oxidized using the quinolinium ion derivative of Example 5. That is, according to the following scheme 3, a compound (hereinafter also referred to as (BNA)$_2$) represented by the following formula (XX) oxidatively was degraded to a compound (hereinafter also referred to as BNA$^+$) represented by the following formula (XXX). Specifically, it is as follows.

Scheme 3

[Chemical Formula 22]

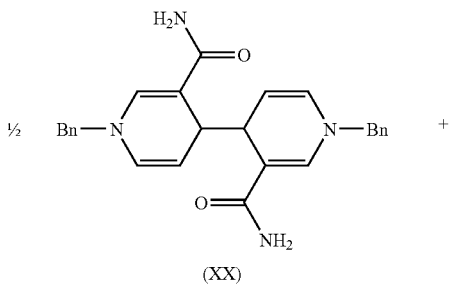

(XX)

(or (BNA)$_2$)

Bn = Benzyl Group

-continued

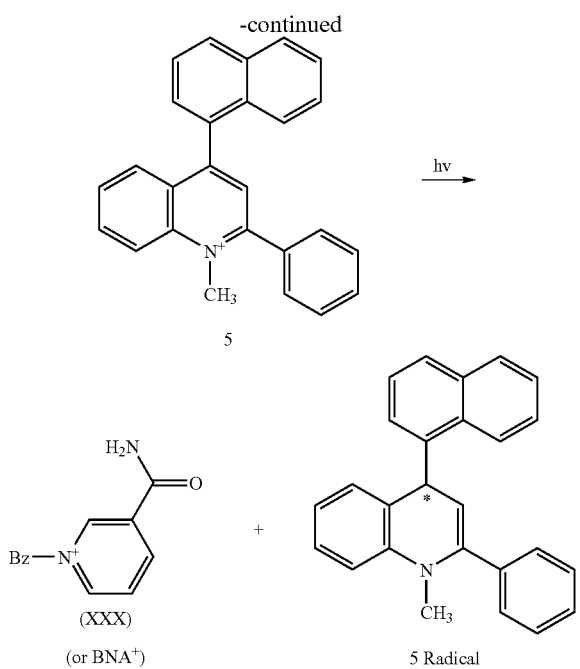

That is, first, both (BNA)$_2$ and perchlorate of the 2-phenyl-4-(1-naphthyl)quinolinium ion (quinolinium ion derivative 5) synthesized as described above were dissolved in deoxygenated acetonitrile and thereby a mixed solution of 2-phenyl-4-(1-naphthyl)quinolinium ion was obtained. The concentration of the mixed solution was set so that the 2-phenyl-4-(1-naphthyl)quinolinium ion concentration was 0.13 mM and the (BNA)$_2$ concentration was 0.070 mM ($7.0\times10^{-5}$ M). Subsequently, the mixed solution was irradiated with a xenon lamp at 298 K (25° C.) and thereafter, the absorbance (transient absorption spectrum) was measured 60 microseconds after irradiation. As a result, absorptions that were considered to originate from BMA$^+$ were generated at 420 nm and 510 nm. Thus, it was proved that (BNA)$_2$ had been oxidatively degraded to BNA$^+$.

Furthermore, the same measurements also were carried out with respect to the quinolinium ion derivatives of Examples 1 to 4, and thereby similar phenomena to that described above were observed.

As described above, in this example, the quinolinium ion derivatives of Examples 1 to 5 were used for oxidants of the present invention and thereby substances to be oxidized were oxidized. Furthermore, in this example, as described above, the quinolinium ion derivatives each were excited through photoirradiation performed with respect to the mixed solution of a quinolinium ion derivative and a substance to be oxidized. Thereafter, the substance to be oxidized was reduced through electron transfer from the substance to be oxidized to the excited species (charge-separated state). Accordingly, this example also is an example of the oxidation method according to the present invention.

INDUSTRIAL APPLICABILITY

As described above, the present invention can provide electron donor-acceptor dyads that can provide a charge-separated state with longevity and not only high oxidizing power but also high reducing power and processes for producing the same. The products of the present invention, that is, photocatalysts, photosensitizers, dyes, oxidants, reductants, cells, dye-sensitized solar cells, and organic EL devices of the present invention can exhibit their excellent functions through generation of such a charge-separated state as described above. Furthermore, the reduction and oxidation methods of the present invention can be performed easily and also are applicable to substances to be reduced that require high reducing power or substances to be oxidized that require high oxidizing power. Moreover, the compounds of the present invention are not limited to the aforementioned applications but are applicable to any applications.

The invention claimed is:

1. The quinolinium ion derivative or salt thereof, represented by any one of the following formula 4 and 5

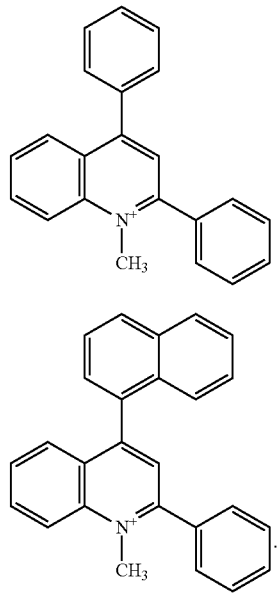

* * * * *